United States Patent
Lin et al.

(10) Patent No.: US 11,851,708 B2
(45) Date of Patent: Dec. 26, 2023

(54) DIAGNOSIS AND TREATMENT OF PSORIATIC ARTHRITIS

(71) Applicant: KAOHSIUNG CHANG GUNG MEMORIAL HOSPITAL, Kaohsiung (TW)

(72) Inventors: Shang-Hung Lin, Kaohsiung (TW); Chih-Hung Lee, Kaohsiung (TW); Chang-Chun Hsiao, Kaohsiung (TW)

(73) Assignee: KAOHSIUNG CHANG GUNG MEMORIAL HOSPITAL, Kaohsiung (TW)

( * ) Notice: Subject to any disclaimer, the term of this patent is extended or adjusted under 35 U.S.C. 154(b) by 0 days.

(21) Appl. No.: 17/535,880

(22) Filed: Nov. 26, 2021

(65) Prior Publication Data
US 2022/0090202 A1   Mar. 24, 2022

Related U.S. Application Data (62) Division of application No. 16/516,663, filed on Jul. 19, 2019, now Pat. No. 11,220,712.

(60) Provisional application No. 62/702,551, filed on Jul. 24, 2018.

(51) Int. Cl.
| | | |
|---|---|---|
| C12Q 1/68 | (2018.01) | |
| C12P 19/34 | (2006.01) | |
| C12Q 1/6883 | (2018.01) | |
| C12N 15/113 | (2010.01) | |
| A61P 19/02 | (2006.01) | |

(52) U.S. Cl.
CPC ............ C12Q 1/6883 (2013.01); A61P 19/02 (2018.01); C12N 15/113 (2013.01); C12N 2310/141 (2013.01); C12Q 2600/118 (2013.01); C12Q 2600/178 (2013.01)

(58) Field of Classification Search
CPC ............ C12Q 1/6883; C12Q 2600/158; C12Q 2600/118; C12Q 2600/141; C12Q 2600/178
See application file for complete search history.

(56) References Cited

FOREIGN PATENT DOCUMENTS

| WO | WO-2008/142567 A2 | 11/2008 |
|---|---|---|
| WO | WO-2013/020926 A1 | 2/2013 |

OTHER PUBLICATIONS

Stephen P. Holly, et al. "Abundance- and Activity-Based Proteomics in Platelet Biology" Curr Proteomics. Oct. 2011; 8(3): 216-228. (Year: 2011).*
Sonkoly et al., "MicroRNAs: Novel Regulators Involved in the Pathogenesis of Psoriasis?" PLoS ONE, Issue 7, Jul. 2007, pp. 1-8, 8 pages.
Nakasa et al., "Expression of MicroRNA-146 in Rheumatoid Arthritis Synovial Tissue," Arthritis & Rheumatism, vol. 58, No. 5, May 2008, 99. 1284-1292, 9 pages.
Pelosi et al., "MicroRNA Expression Profiling in Psoriatic Arthritis," BioMed Research International, vol. 2018, pp. 1-15, 15 pages.
Barcelo et al., "Exosomal microRNAs in seminal plasma are makers of the origin of azoospermia and can predict the presence of sperm in testicular tissue," Human Reproduction, 2018, vol. 33, No. 6, pp. 1087-1098, 12 pages.
Office Action and Search Report corresponding to EP Application No. 19187927.9 dated Nov. 19, 2019. (pp. 10).
Office Action and Search Report corresponding to EP Application No. 19187927.9 dated Mar. 9, 2020. (pp. 10).
Ciancio, G. et al. "Characterisation of peripheral blood mononuclear cell microRNA in early onset psoriatic arthritis." Clinical and Experimental Rheumatology 2017; 35: 113-121 (Year: 2017).

\* cited by examiner

*Primary Examiner* — Stephen T Kapushoc
(74) *Attorney, Agent, or Firm* — Rache Pilloff; Sea Passino; Martin Cosenza (57) ABSTRACT

Methods and kits for diagnosing or predicting the risk of developing psoriatic arthritis in a subject in need of such diagnosis or risk prediction are provided, comprising measuring the expression level of one or more miRNAs disclosed herein in the sample of the subject, and compared the expression level of at least one of the miRNAs in the test sample with that of the psoriatic arthritis-free sample. Also provided are methods of treating psoriatic arthritis by reducing the expression level of at least one of the miRNAs disclosed herein.

11 Claims, 6 Drawing Sheets

Specification includes a Sequence Listing.

DIAGNOSIS AND TREATMENT OF PSORIATIC ARTHRITIS

CROSS-REFERENCE TO RELATED APPLICATION

This application is a Division of pending U.S. patent application Ser. No. 16/516,663, filed on 19 Jul. 2019, which claims the benefit of U.S. Application No. 62/702,551, filed on 24 Jul. 2018, the entire disclosure of which is incorporated herein by reference.

BACKGROUND

Psoriatic arthritis (PsA) is a chronic inflammatory disease involving progressive arthropathy associated with psoriasis. It was estimated that approximately 30% of patients with psoriasis had psoriasis arthritis. Usually, skin manifestations precede the onset of PsA by an average of 10 years. Haroon et al. (Annals of the rheumatic diseases 2015; 74(6):1045-50) reported that diagnostic delay of more than 6 months contributes to the poor radiographic and functional outcome in patients with PsA. Early diagnosis and prompt intervention is critical to prevent permanent joint deformation and destruction. Currently, the diagnosis of PsA is primarily based on clinical phenotype. There is no standardized and reliable assessment method available for early detection of PsA to date, resulting in many patients with psoriasis with undiagnosed PsA and poor treatment outcome. (Veale D J et al., Lancet 2018; 391 (10136):2273-84)

MicroRNAs (miRNAs) are evolutionarily conserved, non-coding RNA molecules that are usually 21-25 nucleotides in length, which function by binding to the 3'-untranslated regions (3'-UTRs) of mRNAs, where they repress protein translation or promote mRNA degradation (See Griffiths-Jones S (2004). The microRNA Registry. *Nucleic acids research* 32: D109-111). Most current studies of miRNAs are at a basic level and further work is needed to establish their clinical applications in psoriatic arthritis.

Consequently, a non-invasive and convenient method to diagnose and predict the risk of psoriatic arthritis and/or treatment of psoriatic arthritis are needed and the present invention satisfy these needs and other needs.

BRIEF SUMMARY OF THE INVENTION

In one embodiment, the present invention provides methods for detecting psoriatic arthritis or predicting the risk of developing psoriatic arthritis in a subject, comprising the step of measuring the expression level of at least one miRNA selected from the group consisting of miR-146a-5p (SEQ ID NO:1) and miR-941 (SEQ ID NO:2) in the test sample of the subject, where in the miRNA is expressed in the extracted CD14+ monocyte or osteoclast of the test sample and a higher expression level of at least one miRNA in the test sample, relative to the expression level of at least one corresponding miRNA in a psoriatic arthritis-free sample, is indicative of the subject having psoriatic arthritis or has a risk of developing psoriatic arthritis.

In another embodiment, the present invention provides methods for detecting psoriatic arthritis and treating psoriatic arthritis in a subject, comprising the step of (a) measuring the expression level of at least one miRNA selected from the group consisting of miR-146a-5p (SEQ ID NO:1) and miR-941 (SEQ ID NO:2) in the test sample of the subject, wherein the miRNA is expressed in the extracted CD14+ monocyte or osteoclast of the test sample and a higher expression level of at least one miRNA in the test sample, relative to the expression level of the at least one corresponding miRNAs in a psoriatic arthritis-free sample, is indicative of the subject having psoriatic arthritis; and (b) administering to the subject a therapeutic agent to treat psoriatic arthritis.

The present invention also provides kits for detecting psoriatic arthritis or predicting the risk of developing psoriatic arthritis in a subject, comprising: (a) at least one microbead to extract CD14+ monocyte from the sample of the subject; and (b) an agent for sequencing or measuring the expression level of at least one miRNA selected from the group consisting of miR-146a-5p and miR-941.

In an exemplary embodiment, the kit further comprises a culture medium comprising M-CSF, RANKL and TNF-α.

Also provided are methods for treating psoriatic arthritis, comprising the step of administering an effective amount of a miR-146a-5p inhibitor complementary to a miRNA at least 90% identical to SEQ ID NO: 1 or a miR-941 inhibitor complementary to a miRNA at least 90% identical to SEQ ID NO:2 to a subject in need thereof.

Methods for determining the efficacy of a therapy for treating psoriatic arthritis in a subject are also disclosed, said method comprising a) measuring the level of expression of at least one miRNA selected from the group consisting of miR-146a-5p and miR-941 in the extracted CD14+ monocyte from the first sample obtained from the subject prior to providing at least a portion of the therapy to the subject, and b) measuring the level of expression of at least one corresponding miRNA in step (a) in the extracted CD14+ monocyte from the second sample obtained from the subject after providing at least a portion of the therapy to the subject, wherein a decrease level of expression of at least one miRNA in the extracted CD14+ monocyte from the second sample relative to the expression level of the corresponding miRNA in the extracted CD14+ monocyte from the first sample, is an indication that the therapy is efficacious to treat psoriatic arthritis.

BRIEF DESCRIPTION OF THE DRAWINGS

Illustrative embodiments of the present invention are described in detail below with reference to the following Figures.

Panels A and B of FIG. 2 show the number of tender joints and the number of swollen joints in 11 PsA patients prior to and after 6 months of treatment. Panels C and D of FIG. 2 illustrate the expression of miR-146a-5p and miR-941 in extracted CD14+ monocytes of normal control (NC), 11 PsA patients prior to (PsA (0)) and after 6 months of treatment (PsA (28 weeks)).

DETAILED DESCRIPTION OF THE INVENTION

As used herein, the articles "a" and "an" refer to one or more than one (i.e., at least one) of the grammatical object of the article.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

"Patient" or "subject" as used herein refers to a mammalian subject diagnosed with or suspected of having or has a risk of developing psoriatic arthritis. Exemplary subjects may be humans, apes, dogs, pigs, cattle, cats, horses, goats, sheep, rodents and other mammalians that can develop psoriatic arthritis.

As used herein interchangeably, a "microRNA," "miR," or "miRNA" refers to the unprocessed (e.g., precursor) or processed (e.g., mature) RNA transcript from a miR gene. MicroRNAs are endogenous non-coding single-stranded RNAs that negatively regulate gene expression in eukaryotes and constitute a novel class of gene regulators (Chua, et al. (2009) Curr. Opin. Mol. Ther. 11:189-199). Individual miRNAs have been identified and sequenced in different organisms, and they have been given names. Names of miRNAs and their sequences are provided herein.

All numbers herein may be understood as modified by "about." As used herein, the term "about," when referring to a measurable value a temporal duration and the like or a range, is meant to encompass variations of ±10% from the specified value, as such variations are appropriate to expression of miRNA level unless otherwise specified.

A "higher" miRNA expression is a relative term and can be determined by comparison of the miRNA expression level in the test sample to that from a referenced pool of healthy individuals known to be psoriatic arthritis free (i.e., normal control).

The term "sample" as used herein refers to a sample that comprises a miRNA. The sample can be utilized for the detection of the presence and/or expression level of a miRNA of interest. Extracted CD14+ monocyte is used with the methods of the presently claimed subject matter, although biological fluids and organs that would be predicted to contain differential expression of miRNAs as compared to normal controls are best suited. In some embodiments, the sample is a relatively easily obtained, such as for example blood or a component thereof. Non limiting examples of the sample include body fluid (e.g. peripheral blood), cells (e.g., CD14+ monocytes or osteoclasts) or tissue (e.g., biopsy specimen or joint fluid).

Measuring the level of miRNA expression refers to quantifying the amount of miRNA present in a sample. Measuring the expression level of a specific, or any miRNA, can be achieved using any method known to those skilled in the art or described herein, such as by real-time PCR, Northern blot analysis. Measuring the expression level of miRNA includes measuring the expression of either a mature form of miRNA or a precursor form that is correlated with miRNA expression.

In a particular embodiment, the level of at least one miRNA is quantified using Northern blot analysis. For example, total cellular RNA can be purified from cells by homogenization in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques and transferred to nitrocellulose filters. The RNA is then immobilized on the filters by heating. Detection and quantification of specific RNA is accomplished using appropriately labeled DNA or RNA probes complementary to the RNA in question. See, for example, Molecular Cloning: A Laboratory Manual, J. Sambrook et al., eds., 2nd edition, Cold Spring Harbor Laboratory Press, 1989, Chapter 7, the entire disclosure of which is incorporated by reference.

In some embodiments, use of a microarray is desirable. A microarray is a microscopic, ordered array of nucleic acids, proteins, small molecules, cells or other substances that enables parallel analysis of complex biochemical samples. The technique provides many oligonucleotides or polynucleotides with known sequence information as probes to find and hybridize with the complementary strands in a sample to thereby capture the complementary strands by selective binding. The probe comprises an oligonucleotide or a polynucleotide sequence that is complementary, or essentially complementary, to at least a portion of the target miRNA sequence. "Complementary" refers to the broad concept of sequence complementarity between regions of two nucleic acid strands. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

Microarray analysis of miRNAs, for example, can be accomplished according to any method known in the art. In one embodiment, RNA is extracted from a cell such as CD14+ monocyte of a sample, the small RNAs (18-26-nucleotides) are size-selected from total RNA using denaturing polyacrylamide gel electrophoresis. Oligonucleotide linkers are attached to the 5' and 3' ends of the small RNAs and the resulting ligation products are used as templates for an RT-PCR reaction with 10 cycles of amplification. The sense strand PCR primer has a fluorophore attached to its 5' end, thereby fluorescently labeling the sense strand of the PCR product. The PCR product is denatured and then hybridized to the microarray. A PCR product, referred to as the target nucleic acid that is complementary to the corresponding miRNA capture probe sequence on the array will hybridize, via base pairing, to the spot at which the capture probes are affixed. The spot will then fluoresce when excited using a microarray laser scanner. The fluorescence intensity of each spot is then evaluated in terms of the number of copies of a particular miRNA, using a number of positive and negative controls and array data normalization methods, which will result in assessment of the level of expression of a particular miRNA. With regard to miRNAs disclosed herein, the probe can be 100% complementary with the target miRNA or polynucleotide sequence. However, the probe need not necessarily be completely complementary to the target polynucleotide along the entire length of the target polynucleotide so long as the probe can bind the target polynucleotide with specificity and capture it from the sample. In some embodiments, the probe is complementary to a polynucleotide at least 90%, at least 95% or 100% identical to SEQ ID NO: 1 or SEQ ID NO:2.

In some embodiments, use of quantitative RT-PCR is desirable. Quantitative RT-PCR (qRT-PCR) is a modification of polymerase chain reaction used to rapidly measure the quantity of a product of polymerase chain reaction. qRT-PCR is commonly used for the purpose of determining whether a genetic sequence, such as a miRNA, is present in a sample, and if it is present, the number of copies in the sample. Any method of PCR that can determine the expression of a nucleic acid molecule, including a miRNA, falls within the scope of the present disclosure. There are several variations of the qRT-PCR method known in the art, include, but are not limited to, via agarose gel electrophoresis, the use of SYBR Green (a double stranded DNA dye), and the use of a fluorescent reporter probe.

The identification of miRNAs that are differentially expressed in psoriatic arthritis and psoriatic arthritis-free subjects, allows the use of this information in a number of ways. For example, a particular treatment regime may be evaluated (e.g., to determine whether a therapy is effective in a subject with psoriatic arthritis). The diagnosis of psoriatic arthritis may be done or confirmed by comparing the miRNA expression level in the extracted CD14+ monocyte or osteoclast of a test sample with the known miRNA expression profile in the extracted CD14+ monocyte or osteoclast of non-psoriatic arthritis samples. Furthermore, multiple determinations of one or more diagnostic or prognostic miRNA levels can be made, and a temporal change in the levels can be used to determine a diagnosis, prognosis or relapse. For example, specific miRNA level(s) can be determined at an initial time, and again at a second time. In some embodiments, an increase in the miRNA level(s) from the initial time to the second time can be diagnostic of the psoriatic arthritis, or a given prognosis. Likewise, a decrease in the miRNA level(s) from the initial time to the second time can be indicative of remission of psoriatic arthritis, or a given prognosis. Furthermore, the degree of change of one or more miRNA level(s) can be related to the severity of the psoriatic arthritis.

In another embodiment, a method for determining the efficacy of a therapy for treating psoriatic arthritis in a subject is provided, said method comprising the steps of comparing: a) the level of expression of at least one miRNA selected from the group consisting of miR-146a-5p and miR-941 in the extracted CD14+ monocyte of a first sample obtained from the subject prior to providing at least a portion of a therapy to the subject, and b) the level of expression of at least one corresponding miRNA in step (a) in the extracted CD14+ monocyte of a second sample obtained from the subject after providing at least a portion of the therapy to the subject, wherein a decreased level of expression of at least one miRNAs in the second sample relative to the expression level of the corresponding miRNA in the first sample, is an indication that the therapy is efficacious for treating psoriatic arthritis. In an exemplary embodiment, the sample is extracted CD14$^+$ monocyte and the miRNA is miR-146a-5p, miR-941 or a combination thereof.

Figure 1A:
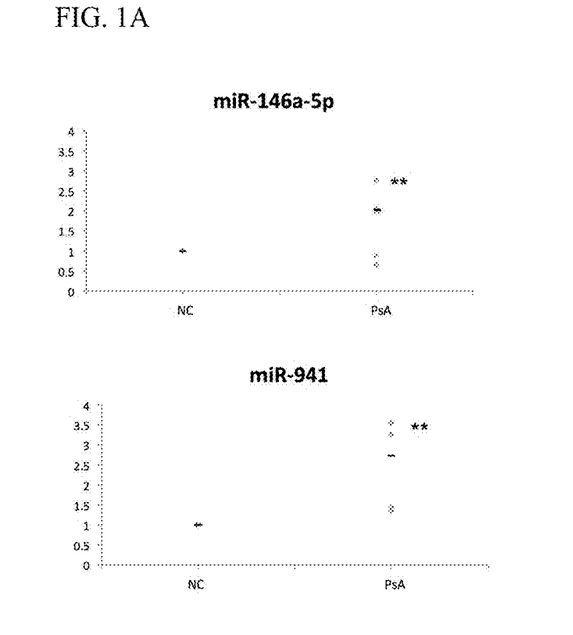
FIG. 1A is an assembly of bar graphs showing the expression levels of miR-146a-5p and miR-941 in the extracted $CD14^+$ monocytes of the normal control (NC) and patients with Psoriatic Arthritis (PsA).
Figure 1B:
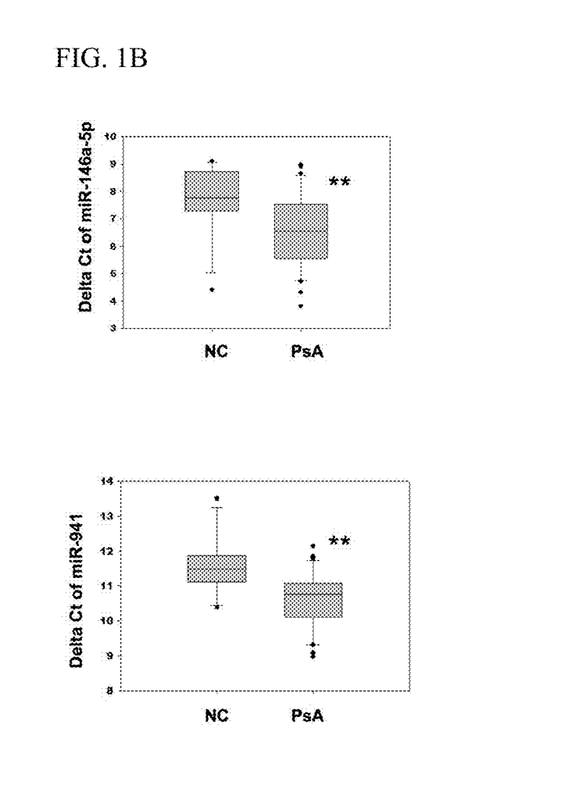
FIG. 1B is an assembly of bar graphs showing the delta Ct values of miR-146a-5p and miR-941.
Figure 1C:
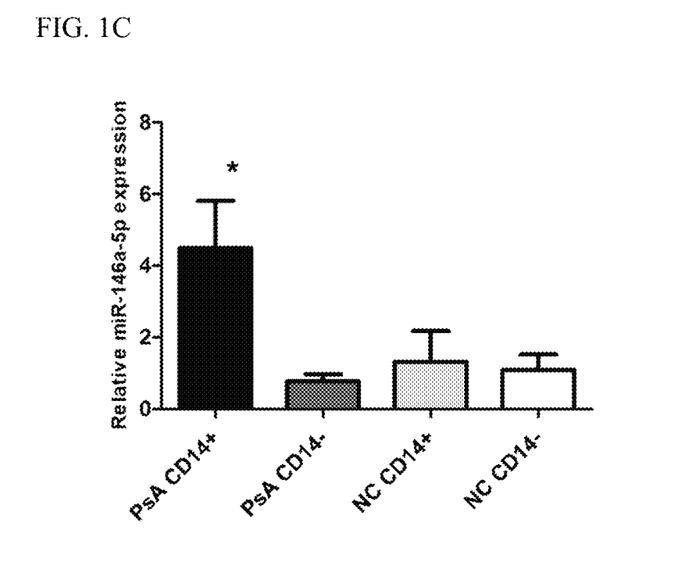
FIG. 1C and FIG. 1D are bar graphs showing the expression of miR 146a-5p and miR-941 in the extracted $CD14^+$ monocytes from normal control (CD14+ NC) and patients with Psoriatic Arthritis (PsA CD14+) and in the peripheral mononuclear cells from the normal control (CD14− NC) and patients with Psoriatic Arthritis (PsA CD14−).
Figure 1D:
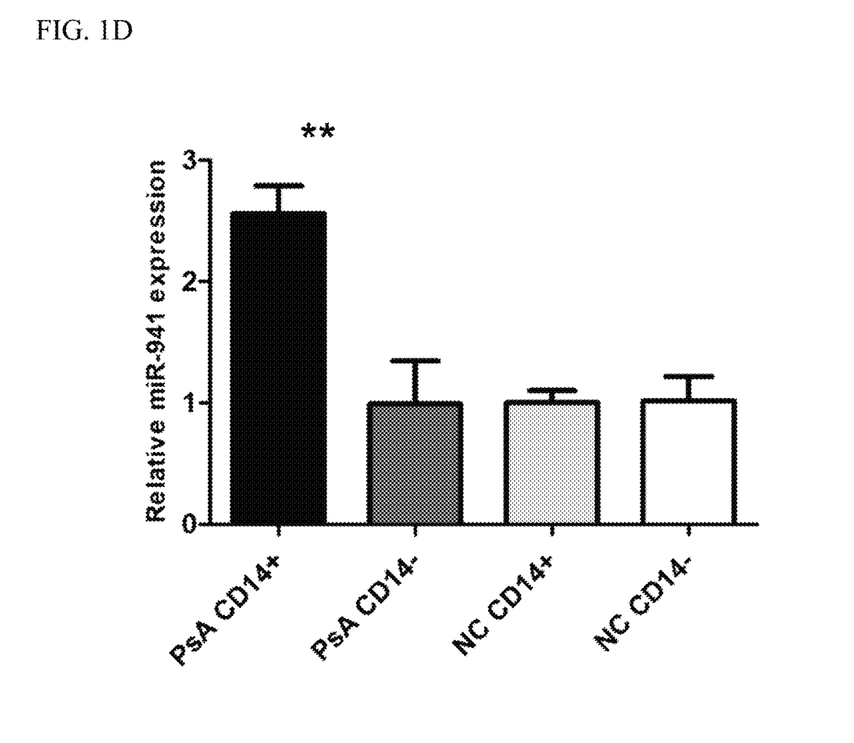

Without being bound by any particular theory, the expression levels of miR-146a-5p and miR-941 are only elevated in the extracted CD14+ monocytes or osteoclasts from a PsA patient, not in peripheral mononuclear cells of PsA subjects, see FIG. 1C and FIG. 1D. Therefore, measuring the expression level of miR-146a-5p, miR-941 or a combination thereof in the peripheral mononuclear cells other than CD14+ monocytes does not provide the diagnosis of PsA. The one or more osteoclast can be osteoclasts differentiated from one or more CD14+ monocyte or from the joint fluid of a PsA patient.

In one embodiment, the kit comprises at least one agent for sequencing or measuring the expression level of at least one miRNA selected from the group consisting of miR-146a-5p and miR-941 in a sample of a subject in need of a diagnosis of or predicting the risk of developing psoriatic arthritis.

In yet another embodiment, the kit further comprises a culture medium comprising M-CSF, RANKL and TNF-α. The culture medium is used to differentiate extracted CD14+ monocytes into osteoclasts.

In an exemplary embodiment, the agent is RT-PCR. In another exemplary embodiment, the kit comprises at least one miRNA-specific oligonucleotide probe that is complementary to an oligonucleotide at least 90%, 95%, or 100% identical to SEQ ID NO: 1 or SEQ ID NO: 2.

"Identical" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

Methods for detecting psoriatic arthritis in a subject are provided, comprising the step of measuring the expression level of at least one of the following miRNA in the test sample of the subject: miR-146a-5p and miR-941, wherein a higher expression level of at least one miRNA in the test sample, relative to the expression level of at least one corresponding miRNA in a psoriatic arthritis-free sample, is indicative of the subject having psoriatic arthritis or has a risk of developing psoriatic arthritis.

The present invention further provides method for detecting and treating psoriatic arthritis in a subject, comprising the step of (a) measuring the expression level of at least one of the following miRNA in the test sample of the subject: miR-146a-5p and miR-941, wherein a higher expression level of at least one miRNA in the test sample, relative to the expression level of at least one corresponding miRNA in a psoriatic arthritis-free sample, is indicative of the subject having psoriatic arthritis or has a risk of developing psoriatic arthritis; and (b) administering a therapeutic agent to treat psoriatic arthritis. Non limiting examples of the therapeutic agent include nonsteroidal anti-inflammatory drugs (NSAIDs), disease-modifying anti-rheumatic, drugs (DMARDs), immunosuppressants, TNF-alpha inhibitors, apremilast (Otezla), ustekinumab (Stela), secukinumab (Cosentyx), a miR-146a-5p inhibitor or a miR-941 inhibitor disclosed herein, or a combination thereof.

In some embodiments, a method for treating psoriatic arthritis in a subject in need thereof is provided, said method comprises the step of administering a miR-146a-5p inhibitor complementary to a polynucleotide at least 90%, at least 95, or 100% identical to SEQ ID NO: 1 and/or a miR-941 inhibitor complementary to a polynucleotide at least 90%, at least 95, or 100% identical to SEQ ID NO:2 to the subject.

Embodiments of the present invention are illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the invention. During the studies described in the following examples, conventional procedures were followed, unless otherwise stated. Some of the procedures are described below for illustrative purpose.

Example 1

Study Participant: A case control study was conducted to examine the expression of various miRNAs in patients with psoriatic arthritis (case) and healthy normal controls without PsA (NC).

16 healthy normal controls (NC) and 31 patients with PsA (based on the Classification Criteria for Psoriatic Arthritis, CASPAR, Taylor W et al., Arthritis and Rheumatism 2006; 54(8):2665-73) were enrolled in the study.

Next-generation sequencing (NGS) with subsequent validation by quantitative PCR (qPCR) assays were used to explore the potential PsA biomarker. The RNA samples form 2 NC and 4 PsA were used as initial validation of candidate miRNA from the NGS study.

The CD14+ monocytes in the peripheral blood of the enrolled subjects were extracted and isolated by CD14+ MicroBeads (Miltenyi Biotec, Taiwan). The RNA samples were extracted from the isolated CD14+ monocytes, followed by quality examination with Agilent Bioanalyzer 2100 (Agilent, USA) to select RNA samples with a RNA integrity number value ≥8.0. Selected RNA samples were prepared with the TruSeq Small RNA Preparation protocol (Illumina, USA).

RNA libraries from 2 pooled male NCs, 2 pooled female NCs, 2 pooled male patients with PsA and 2 pooled female patients with PsA were sequenced with Illumina NGS platform, followed by miRSeq8 analysis to profile micro (mi)-RNA expressions. The prepared amplicons were sequenced with a V3 150-cycle sequencing reagent on the MiSeq facility (Illumina) to generate 51-nt single-end reads. Clustered analysis was conducted to examine the miRNA expression profiles of PsA and NC samples.

Of the RNA samples examined with NGS, there were approximately 27.7 million raw reads in total and each sample accounted for an average of 6.9 million reads. The generated NGS data was analyzed with miRSeq (Pan C T. et al., Biomed Res Int 2014:462135) for miRNA quantification and sequencing quality evaluation. miRSeq presented miRNA expression levels in terms of transcript per million (TPM). As shown in Table 1, 13 miRNAs with TPM values higher than 1000 in at least one sample and the average expression ratios (normal to disease or disease to normal) were at least 1.5.

TABLE 1

List of miRNA with a higher expression level in PsA patients

| miR_ID | Normal-M | Disease-M | Normal-F | Disease-F |
|---|---|---|---|---|
| ★ hsa-miR-941 | 1808.1 | 4024.4 | 1048.4 | 3160.4 |
| hsa-miR-148b-3p | 4651.1 | 5917.1 | 9504.1 | 24585.1 |
| hsa-miR-501-3p | 417.1 | 269.1 | 959.1 | 2497.1 |
| hsa-miR-148a-3p | 6327.1 | 6491.1 | 5111.1 | 12029.1 |
| hsa-miR-21-3p | 6016.1 | 8318.1 | 4129.1 | 7879.1 |
| hsa-miR-10a-5p | 776.1 | 1154.1 | 646.1 | 1053.1 |
| hsa-miR-146b-5p | 3759.1 | 5421.1 | 3615.1 | 5810.1 |
| hsa-miR-101-3p | 4366.2 | 3236.2 | 3340.2 | 1568.2 |
| hsa-miR-30b-5p | 1752.1 | 1547.1 | 1459.1 | 402.1 |
| hsa-miR-19b-3p | 1323.2 | 1064.2 | 1451.2 | 608.2 |
| hsa-miR-142-3p | 1175.1 | 853.1 | 2056.1 | 1046.1 |
| hsa-miR-340-5p | 5377.1 | 4091.1 | 5263.1 | 2123.1 |
| hsa-miR-20a-5p | 1203.1 | 1087.1 | 2315.1 | 944.1 |

Amongst the 13 miRNAs, the expressions of miR-941 was increased in patients with PsA.

qPCR was performed on 2 NC samples and 4 PsA samples to further validate the NGS data. qPCR analysis showed the expression of miR-941 and miR-146a-5p were increased in patients with PsA as compared to those from NCs (see FIG. 1A).

SVM is a machine learning algorithm for dealing with binary classification problems, such as treatment versus control or disease versus normal. The DCt values of miR-941 and miR-146a-5p in NC and PsA patients shown in FIG. 1B were used to train the SVM classification with a 5-fold cross-validation to eliminate overfitting and underfitting.

FIG. 1C and FIG. 1D show the expressions of miR 146a-5p and miR-941 are increased in the extracted CD14+ monocytes from patients with Psoriatic Arthritis (PsA CD14+) but not in the peripheral mononuclear cells from patients with Psoriatic Arthritis (PsA CD14−).

Table 2 shows the combination of miR-146a-5p and miR-941 lead to an unexpected synergy in sensitivity, specificity and the area under the receiver operating characteristic (auROC) values in PsA diagnosis.

TABLE 2

Sensitivity, specificity and auROC of PsA diagnosis
based on the miR-146a-5p and miR-941 combination

| | Sensitivity | Specificity | auROC |
|---|---|---|---|
| miR-146a-5p | 0.83 | 0.69 | 0.82 |
| miR-941 | 0.87 | 0.81 | 0.81 |
| miR-146a-5p and miR-941 | 1.0 | 0.94 | 0.99 |

The expressions of miR-941 and miR-146a-5p in the extracted CD14+ monocytes from 16 NC and 11 PsA patients were measured prior to and after 6 months of PsA treatment (including adalimumab, etanercept, golimumab, ustekinumab or secukinumab).

Figure 2:
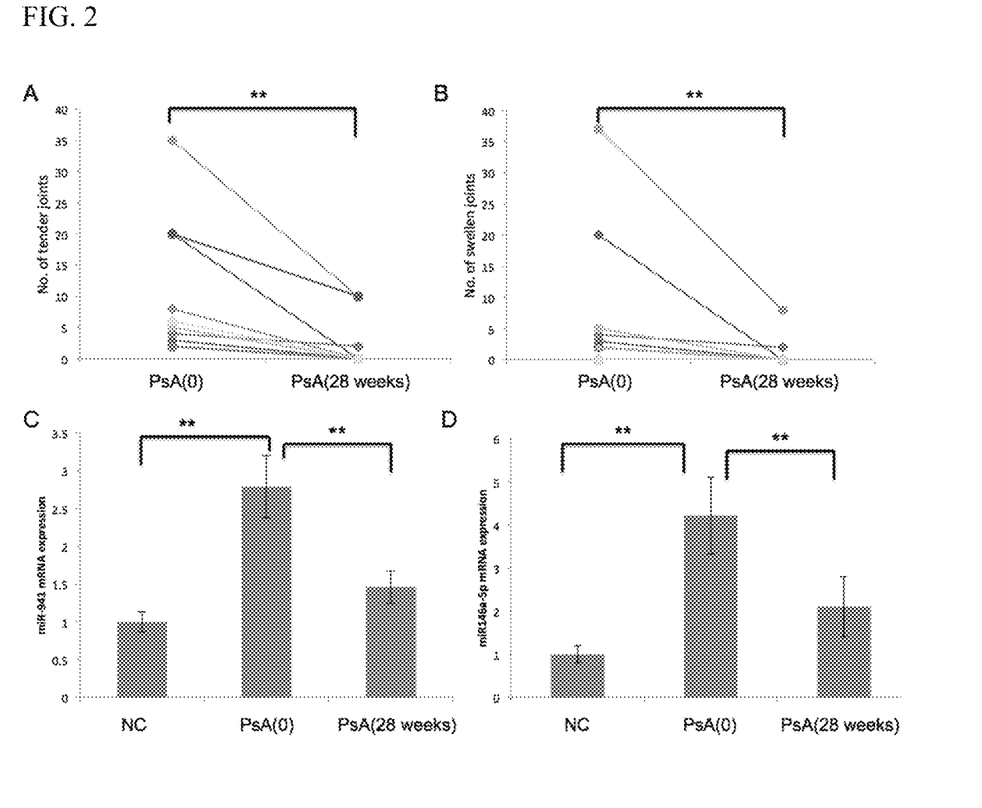

11 PsA patients had significant symptomatic relief (reduced tenderness and swelling of the joints) 28 weeks after the therapy was commenced (see panels A and B of FIG. 2). The expressions of miR-941 and miR-146a-5p in the extracted CD14+ monocytes of 11 PsA patients after 6 months of treatment were significantly reduced (panels C and D of FIG. 2). The decreased expressions of miR-941 and miR-146a-5p in the extracted CD14+ monocytes correlated with symptom relief in the PsA patients.

The expression levels of miR-941 and miR-146a-5p in osteoclasts differentiated from the extracted CD14+ monocytes.

Figure 3A:
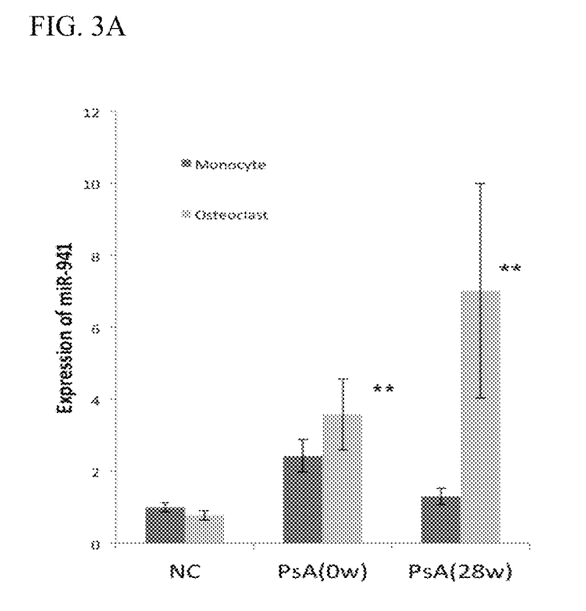
FIG. 3A and FIG. 3B are bar graphs showing the expressions of miR-941 and miR-146a-5p in the $CD14^+$ monocytes derived osteoclasts of the normal control (NC), PsA patients prior to (PsA(0w)) and after 6 months (PsA(28w)) of PsA treatment.
Figure 3B:
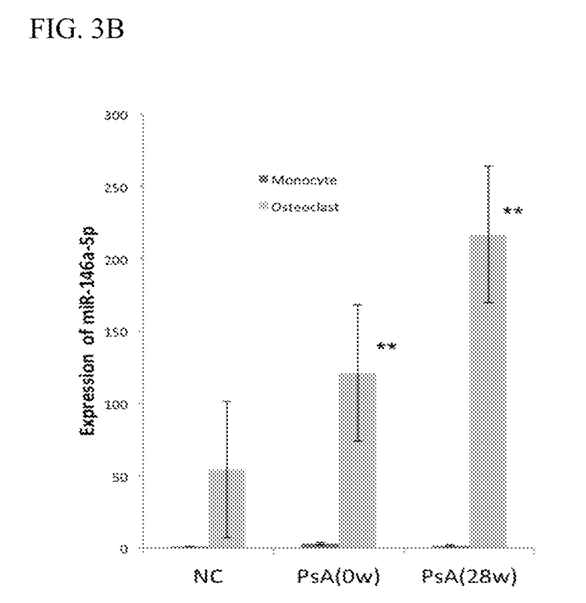

CD14+ monocytes were extracted from the peripheral blood of 2 NCs and 2 PsA patients before and after 6-months of PsA treatment. The extracted CD14+ monocytes were cultured with M-CSF 50 ng/ml for 3 days, followed by 100 ng/ml of RANKL and 100 ng/ml of TNF-α for 9 days for osteoclasts differentiation. Osteoclasts are known to cause joint destruction in PsA. As illustrated in FIG. 3A and FIG. 3B, the expressions of miR-941 and miR-146a-5p in the CD14+ monocytes derived osteoclasts of the PsA patients before and after successful treatment were higher than those of the NCs ($p<0.05$ and $p<0.05$). The results show that expressions of miR-941 and miR-146a-5p in the CD14 monocytes-derived osteoclast are higher regardless of the diseases activity.

Example 2

An in vitro evaluation of the effect of miR-941 inhibitor and miR-146a-5p inhibitor on CD14+ monocytes derived osteoclasts from patients with PsA was performed.

The CD14+ monocytes were extracted from the peripheral blood of PsA patients and cultured with M-CSF for 72 hours. The cultured CD14+ monocytes were treated with the following protocols:

(1) No miRNA transfection: The CD14+ monocytes were cultured with TNF-α and RANKL every 3 days for 9 days to differentiate into osteoclasts.

(2) Negative control mRNA transfection: The CD14+ monocytes were transfected with a negative control miRNA (SEQ ID NO: 3) for 6 hours, then cultured with TNF-α and RANKL every 3 days for 9 days to differentiate into osteoclasts.

(3) miR-941 inhibitor transfection: The CD14+ monocytes were transfected with a miR-941 inhibitor (SEQ ID NO:4) for 6 hours, then cultured with TNF-α and RANKL every 3 days for 9 days to differentiate into osteoclasts.

(4) miR-146a-5p inhibitor transfection: The CD14+ monocytes were transfected with a miR-146a-5p inhibitor (SEQ ID NO:5) for 6 hours, then cultured with TNF-α and RANKL every 3 days for 9 days to differentiate into osteoclasts.

Figure 4A:
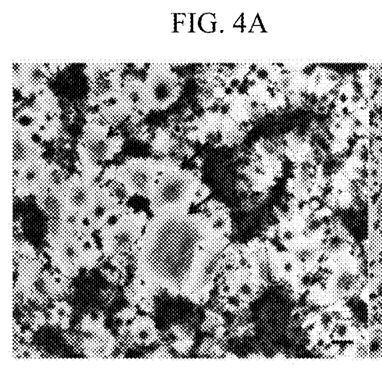
FIG. 4A-4D are an assembly of microscopic images showing the effect of no miR transfection (FIG. 4A), transfection with a negative control miRNA (FIG. 4B), a miR-941 inhibitor (FIG. 4C) or a miR-146a-5p inhibitor (FIG. 4E) on the quantity of CD14+ monocyte derived osteoclasts.
Figure 4B:
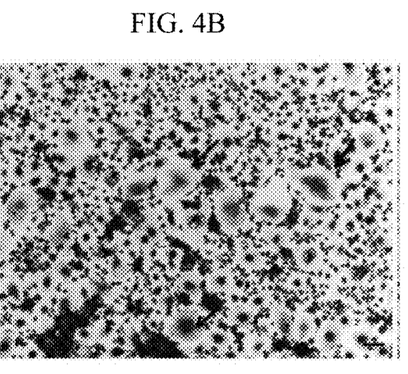
Figure 4C:
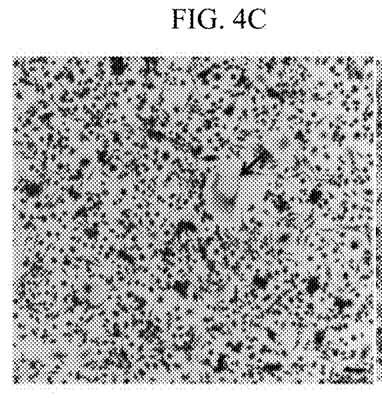
Figure 4D:
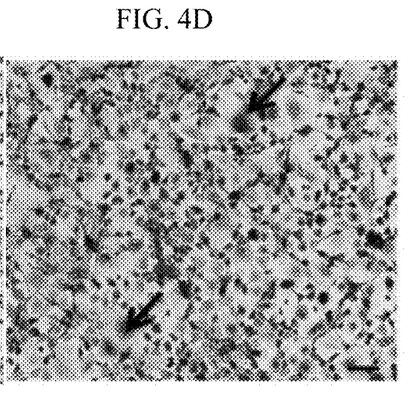
Figure 4E:
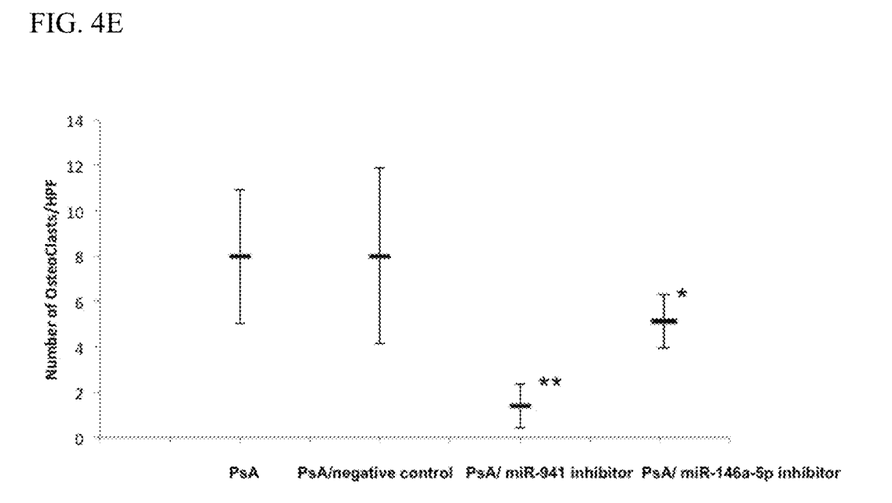
FIG. 4E is a bar graph illustrating the effect of no miR transfection (PsA), transfection with a negative control miRNA, miR-941 inhibitor or a miR-146a-5p inhibitor on the quantity of CD14+ monocyte derived osteoclasts.

As illustrated in FIG. 4A-4E, the miR-941 inhibitor (FIG. 4C) or miR-146a-5p inhibitor (FIG. 4D) significantly decreased the number of CD14+ monocytes derived osteoclasts compared to that of negative control miR transfection (FIG. 4B) and no miR transfection group (FIG. 4A). Therefore, inhibitors of miR-146a-5p or miR-941 reduce osteoclastogenesis in PsA patients and can be used to treat PsA.

Example 3

A case control study included was conducted to examine the expressions of miR146a-5p and miR941 in 40 healthy normal controls (NC), 40 patients with psoriasis without arthritis (PsO) and 40 patients with Psoriatic arthritis (PsA).

Figure 5A:
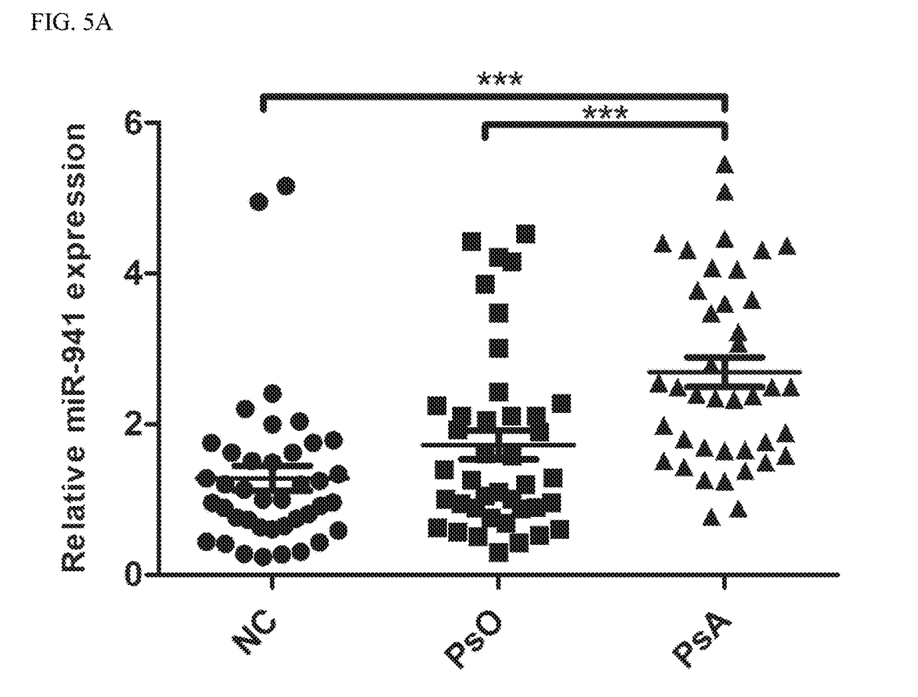
FIG. 5A and FIG. 5B show the expression of miR 146a-5p and miR-941 in the extracted CD14$^+$ monocytes from normal control (NC), patients with psoriasis without arthritis (PsO) and patients with psoriatic arthritis.
Figure 5B:
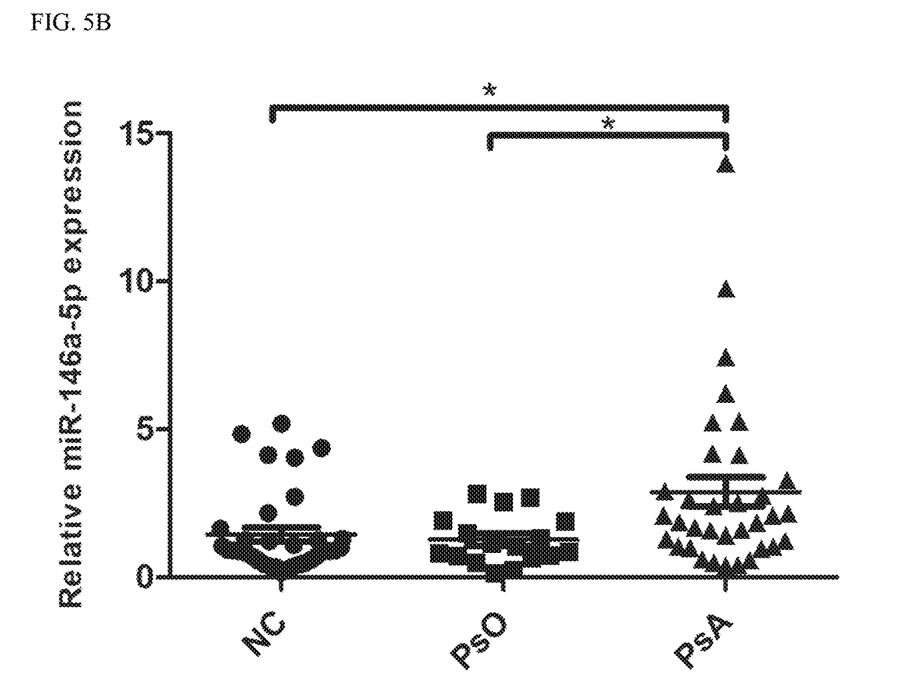

The diagnosis of PsA and the expression of miRNAs were measured according to the criteria and steps in Example 1. FIG. 5A and FIG. 5B show the expression of miR146a-5p and miR941 is significant higher than that of NC and PsO. The results show increased expressions of miR146a-5p and miR941 can predict the risk of developing arthritis in patients with psoriasis.

What is claimed is:

1. A method for detecting or predicting the risk of developing psoriatic arthritis and treating psoriatic arthritis in a subject in need thereof, comprising the step of
   (a) obtaining a test sample from the subject, wherein the subject exhibits one or more symptoms of psoriatic arthritis or is at risk of developing psoriatic arthritis; wherein the test sample comprises CD14+ monocytes or osteoclasts derived from CD14+ monocytes;
   (b) measuring the expression level of miR-146a-5p in the test sample of the subject;
   (c) identifying the subject as having psoriatic arthritis or as having a risk of developing psoriatic arthritis by detecting increased expression level of miR-146a-5p in the test sample relative to the expression level of miR-146a-5p in a psoriatic arthritis-free sample that comprises CD14+ monocytes or osteoclasts derived from CD14+ monocytes; and
   (d) administering to the subject a therapeutic agent to treat psoriatic arthritis.

2. The method of claim 1, wherein the miRNA expression level is determined by real-time PCR.

3. The method of claim 1, wherein the miRNA expression level is determined by an oligonucleotide probe at least 90% complementary to SEQ ID NO: 1.

4. The method of claim 1, further comprising measuring the expression level of miR-941 in the test sample of the subject.

5. The method of claim 4, wherein the miRNA expression level is determined by real-time PCR.

6. The method of claim 4, wherein the miRNA expression level of miR-941 is determined by an oligonucleotide probe at least 90% complementary to SEQ ID NO: 2.

7. The method of claim 1, wherein the therapeutic agent is a miR-146a-5p inhibitor having a nucleotide sequence of at least 90% complementary to SEQ ID NO: 1 or a miR-941 inhibitor having a nucleotide sequence at least 90% complementary to SEQ ID NO:2.

8. The method of claim 1, wherein the therapeutic agent is a nucleotide sequence that is 100% identical to the nucleotide sequence of SEQ ID NO: 5.

9. The method of claim 1, wherein the therapeutic agent is a nucleotide sequence that is 100% identical to the nucleotide sequence of SEQ ID NO: 4.

10. The method of claim 7, wherein the miR-146a-5p inhibitor has a nucleotide sequence that is at least 90% complementary to SEQ ID NO: 1.

11. The method of claim 7, wherein the miR-941 inhibitor having a nucleotide sequence at least 90% complementary to SEQ ID NO:2.

* * * * *

SEQUENCE LISTING

<160> NUMBER OF SEQ ID NOS: 5

<210> SEQ ID NO 1
<211> LENGTH: 22
<212> TYPE: RNA
<213> ORGANISM: Homo sapiens
<220> FEATURE:
<223> OTHER INFORMATION: miR-146a-5p

<400> SEQUENCE: 1
ugagaacuga auuccauggg uu                 22

<210> SEQ ID NO 2
<211> LENGTH: 23
<212> TYPE: RNA
<213> ORGANISM: Homo sapiens
<220> FEATURE:
<223> OTHER INFORMATION: miR-941

```
<400> SEQUENCE: 2
cacccggcug ugugcacaug ugc                                          23

<210> SEQ ID NO 3
<211> LENGTH: 24
<212> TYPE: RNA
<213> ORGANISM: Homo sapiens
<220> FEATURE:
<223> OTHER INFORMATION: Negative control miRNA

<400> SEQUENCE: 3
ucacaaccuc cuagaaagag uaga                                         24

<210> SEQ ID NO 4
<211> LENGTH: 23
<212> TYPE: RNA
<213> ORGANISM: Homo sapiens
<220> FEATURE:
<223> OTHER INFORMATION: miR-941 Inhibitor

<400> SEQUENCE: 4
gugggccgac acacguguac acg                                          23

<210> SEQ ID NO 5
<211> LENGTH: 22
<212> TYPE: RNA
<213> ORGANISM: Homo sapiens
<220> FEATURE:
<223> OTHER INFORMATION: miR-146a-5p Inhibitor

<400> SEQUENCE: 5
acucuugacu uaagguaccc aa                                           22
```